United States Patent
Koo et al.

(10) Patent No.: US 9,615,594 B2
(45) Date of Patent: Apr. 11, 2017

(54) MIXED LACTIC ACID BACTERIAL CULTURE FLUID COMPOSITION FOR DELAYED RIPENING OF KIMCHI AND METHOD FOR MAKING KIMCHI USING SAME

(75) Inventors: Cha-Hak Koo, Seoul (KR); Seung Woo Lee, Seoul (KR); Seung Ho Jang, Seoul (KR); Dong Yun Lee, Gyeonggi-do (KR)

(73) Assignee: OURHOME Co., LTD., Seoul (KR)

( * ) Notice: Subject to any disclaimer, the term of this patent is extended or adjusted under 35 U.S.C. 154(b) by 212 days.

(21) Appl. No.: 14/359,062

(22) PCT Filed: Nov. 29, 2011

(86) PCT No.: PCT/KR2011/009173
§ 371 (c)(1),
(2), (4) Date: Sep. 22, 2014

(87) PCT Pub. No.: WO2013/073733
PCT Pub. Date: May 23, 2013

(65) Prior Publication Data
US 2015/0050407 A1 Feb. 19, 2015

(30) Foreign Application Priority Data

Nov. 17, 2011 (KR) .................. 10-2011-0120210

(51) Int. Cl.
*A23B 7/154* (2006.01)
*A23L 1/218* (2006.01)
*A23B 7/10* (2006.01)
*C12N 1/20* (2006.01)
*C12P 39/00* (2006.01)
*A23L 19/20* (2016.01)

(52) U.S. Cl.
CPC ............. *A23B 7/154* (2013.01); *A23B 7/10* (2013.01); *A23L 19/20* (2016.08); *C12N 1/20* (2013.01); *C12P 39/00* (2013.01); *A23V 2002/00* (2013.01)

(58) Field of Classification Search
CPC ................................ A23B 7/154; A23L 1/218
USPC ........................................................ 426/532
See application file for complete search history.

(56) References Cited

U.S. PATENT DOCUMENTS

| 5,869,116 | A * | 2/1999 | Yoo ............ A23B 7/10 426/49 |
| 2007/0117193 | A1 * | 5/2007 | Park ............ C12N 1/20 435/139 |

FOREIGN PATENT DOCUMENTS

| JP | 2005-512591 | 5/2005 |
| JP | 2009-082010 | 4/2009 |
| JP | 2014-542214 | 11/2011 |
| KR | 10-1997-0006116 | 4/1997 |
| KR | 10-1998-0030454 | 7/1998 |
| KR | 10-0181009 | 2/1999 |
| KR | 10-1999-0061707 | 7/1999 |
| KR | 10-0266373 | 9/2000 |
| KR | 10-2003-0008249 | 1/2003 |
| KR | 10-2005-0066427 | 6/2005 |
| KR | 10-2007-0071911 | 4/2007 |
| KR | 10-2010-0099537 | 9/2010 |
| KR | 10-2011-0044548 | 4/2011 |
| WO | 2010/074465 | 7/2010 |

OTHER PUBLICATIONS

Lee, J-S, et al. Int. J. Food Microbiol. 102: 143-150 (2005).*
Lee et al. Food Sci. Biotechnol. 19: 641-646 (2010).*
Chang, J.Y. et al., "Improvements in the quality and shelf life of Kimchi by fermentation with the induced bacteriocin-producing strain, leuconostoc citreum Gj7 as a starter" Journal of Food Science, vol. 75, No. 2, pp. M103-M110, (2010).
International Search Report dated Nov. 23, 2012 for PCT application No. PCT/KR2011/009173.

\* cited by examiner

*Primary Examiner* — Hamid R Badr
(74) *Attorney, Agent, or Firm* — Evan Law Group LLC

(57) ABSTRACT

Provided are: a culture fluid composition for delaying the ripening of kimchi, which contains a mixed lactic acid bacterial culture fluid with which a culture fluid containing six types of lactic acid bacteria is mixed to be capable of specifically inhibiting the proliferation of lactic acid bacteria in fermented kimchi; vitamin B1; and lactic acid and a method for making kimchi using same for delaying the ripening of kimchi.

6 Claims, 6 Drawing Sheets

MIXED LACTIC ACID BACTERIAL CULTURE FLUID COMPOSITION FOR DELAYED RIPENING OF KIMCHI AND METHOD FOR MAKING KIMCHI USING SAME

TECHNICAL FIELD

The present invention relates to a culture fluid composition for delaying fermentation of kimchi and a method of making kimchi using the same.

BACKGROUND ART

Kimchi is a traditional fermented Korean food made by mixing salted vegetables, such as Chinese cabbages, with spices and seasonings, such as red pepper powder and salted fish or seafood sauce, and fermenting the mixture at a low temperature. The nutritional excellence of kimchi has been recently recognized internationally. However, kimchi is a fermented product at a low temperature and thus involves quality variation by environmental changes during distribution, deteriorating product value.

Extensive studies are being conducted from various angles to solve such problems. For example, methods of adopting lactic acid bacteria with excellent antibiotic activity, a lactic acid bacteria starter having low acid generation performance, and natural extracts are used to delay maturation of kimchi.

A method of adopting lactic acid bacteria with excellent antibiotic activity, which generally uses a single species of lactic acid bacteria, has a narrow antibacterial spectrum and thus provides limited effects. A method of adopting a lactic acid bacteria starter having low acid generation performance also has a limitation in the starter forming a dominant species. Methods of using natural extracts spoil unique flavors and tastes of kimchi, thus deteriorating product value.

Thus, the inventors of the present invention achieve a kimchi making method capable of delaying maturation of kimchi while maintaining unique tastes and flavors of kimchi.

DISCLOSURE OF INVENTION

Technical Goals

An aspect of the present invention provides a method of making kimchi which is capable of delaying maturation of kimchi fermented at a low temperature to hardly change quality of kimchi despite environmental changes in food distribution and storage, thus maintaining product value for a long time.

Technical Solutions

According to an aspect of the present invention, there is provided a culture fluid composition for delaying maturation of kimchi including a mixed lactic acid bacteria (LAB) culture fluid prepared by mixing culture media obtained by culturing *Lactobacillus plantarum, Pediococcus pentosaceus, Lactobacillus casei, Lactobacillus paracasei, Lactobacillus sakei* and *Leuconostoc citreum*; vitamin B1; and lactic acid.

The *Lactobacillus plantarum* is *Lactobacillus plantarum* OH22 with an accession number of KCTC12058BP, deposited in the Korean Collection for Type Cultures as of Nov. 8, 2011. The *Pediococcus pentosaceus* is *Pediococcus pentosaceus* OH19 with an accession number of KCTC12057BP, deposited in the Korean Collection for Type Cultures as of Nov. 8, 2011. The *Lactobacillus casei* is *Lactobacillus casei* OH12 with an accession number of KCTC12055BP, deposited in the Korean Collection for Type Cultures as of Nov. 8, 2011. The *Lactobacillus paracasei* is *Lactobacillus paracasei* OH14 with an accession number of KCTC12056BP, deposited in the Korean Collection for Type Cultures as of Nov. 8, 2011. The *Lactobacillus sakei* is *Lactobacillus sakei* OK1 with an accession number of KCTC12059BP, deposited in the Korean Collection for Type Cultures as of Nov. 8, 2011. The *Leuconostoc citreum* is *Leuconostoc citreum* OK2 with an accession number of KCTC12060BP, deposited in the Korean Collection for Type Cultures as of Nov. 8, 2011.

The mixed LAB culture fluid may include the culture media of *Lactobacillus plantarum, Pediococcus pentosaceus, Lactobacillus casei, Lactobacillus paracasei, Lactobacillus sakei* and *Leuconostoc citreum* in the same amount.

The culture fluid composition may include 1 to 40 parts by weight of vitamin B1 and 5 to 40 parts by weight of lactic acid based on 100 parts by weight of the mixed LAB culture fluid.

According to another aspect of the present invention, there is provided a method of making maturation-delayed kimchi including salting Chinese cabbage; and mixing the salted Chinese cabbage with a culture fluid composition and a seasoning selected from the group consisting of white radish, onion, red pepper powder, garlic, ginger, spring onion, white sugar and salted shrimp sauce, wherein the culture fluid composition includes a mixed LAB culture fluid, vitamin B1 and lactic acid.

The mixed LAB culture fluid may be prepared by mixing culture media obtained by culturing *Lactobacillus plantarum, Pediococcus pentosaceus, Lactobacillus casei, Lactobacillus paracasei, Lactobacillus sakei* and *Leuconostoc citreum*. The culture fluid composition may include 1 to 40 parts by weight of vitamin B1 and 5 to 40 parts by weight of lactic acid based on 100 parts by weight of the mixed LAB culture fluid.

Advantageous Effects

According to the present invention, growth of kimchi fermentation lactic acid bacteria (LAB) is inhibited to minimize generation of acid by the LAB, thereby delaying maturation of kimchi and accordingly enhancing storage of kimchi. Maturation-delayed kimchi according to a making method of the present invention may minimally change in quality during distribution to provide a savory flavor for a longer time, thus being appropriate for not only domestic distribution but export.

BEST MODE FOR CARRYING OUT THE INVENTION

Figure 1:
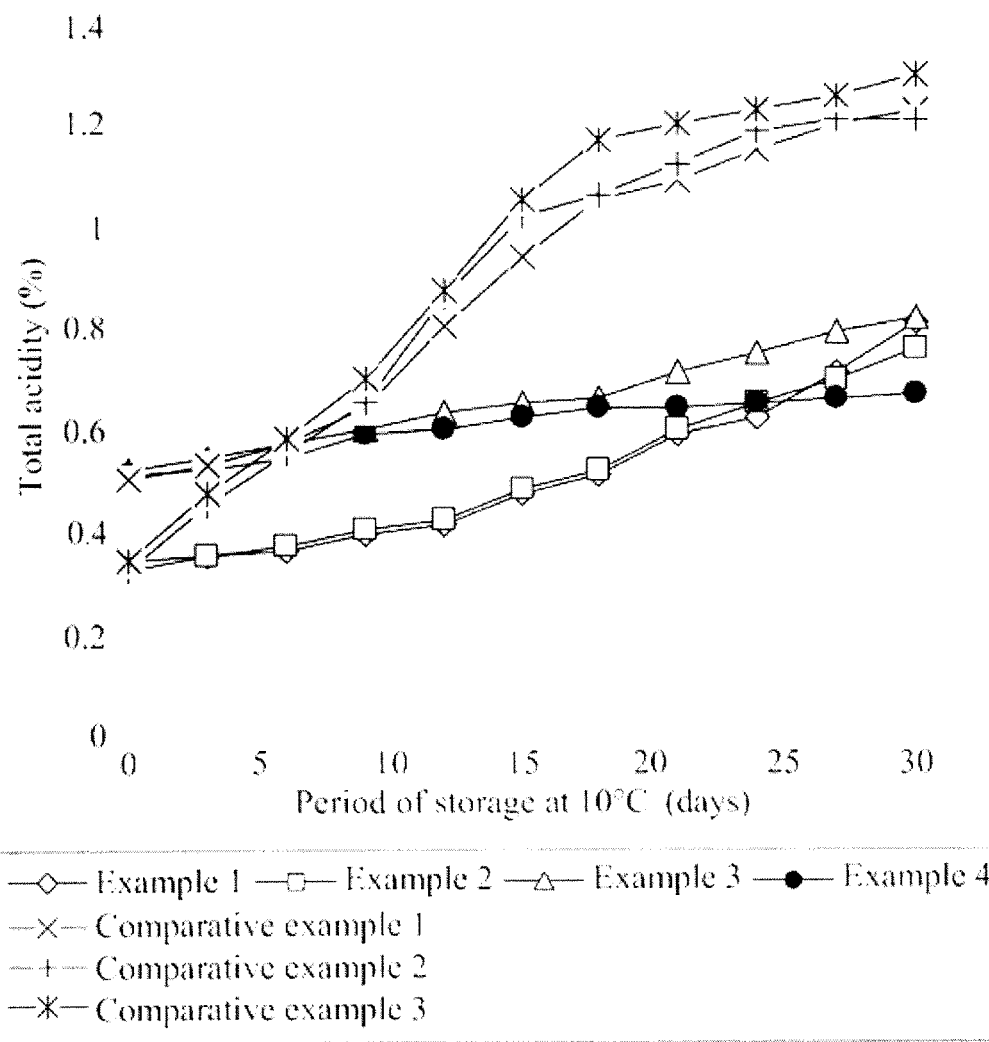
FIG. 1 is a graph illustrating acidities of kimchi products mixed with compositions according to Examples 1 to 4 and Comparative Examples 1 to 3 stored at 10° C. for 30 days.

A culture fluid composition for delaying maturation of kimchi according to an embodiment of the present invention includes a mixed lactic acid bacteria (LAB) culture fluid, vitamin B1 and lactic acid, wherein the mixed LAB culture fluid includes six types of LAB capable of specifically inhibiting proliferation of LAB in fermented kimchi, such as *Lactobacillus plantarum, Pediococcus pentosaceus, Lactobacillus casei, Lactobacillus paracasei, Lactobacillus sakei* and *Leuconostoc citreum*.

The culture fluid composition for delaying maturation of kimchi may include 1 to 40 parts by weight of vitamin B1 and 5 to 40 parts by weight of lactic acid based on 100 parts by weight of the mixed LAB culture fluid and exhibit an optimal effect of delaying maturation of kimchi by adding vitamin B1 and lactic acid to the mixed LAB culture fluid.

The mixed LAB culture fluid may include the culture media of *Lactobacillus plantarum, Pediococcus pentosaceus, Lactobacillus casei, Lactobacillus paracasei, Lactobacillus sakei* and *Leuconostoc citreum* in the same amount.

A method of making maturation-delayed kimchi according to an exemplary embodiment of the present invention includes salting Chinese cabbage; and mixing the salted Chinese cabbage with a culture fluid composition and a seasoning selected from the group consisting of white radish, onion, red pepper powder, garlic, ginger, spring onion, white sugar and salted shrimp sauce, wherein the culture fluid composition includes a mixed LAB culture fluid, vitamin B1 and lactic acid.

The mixed LAB culture fluid may be prepared by mixing culture media obtained by culturing six types of LAB capable of specifically inhibiting proliferation of LAB in fermented kimchi, such as *Lactobacillus plantarum, Pediococcus pentosaceus, Lactobacillus casei, Lactobacillus paracasei, Lactobacillus sakei* and *Leuconostoc citreum*. The culture fluid composition may include 1 to 40 parts by weight of vitamin B1 and 5 to 40 parts by weight of lactic acid based on 100 parts by weight of the mixed LAB culture fluid.

Although the present invention will be described in detail with reference to the following examples, these examples are not to be in any way construed as limiting the present invention.

EXAMPLES

Isolation of Vegetable LAB

Ten kinds of kimchi products made by ordinary kimchi recipes were selected for use as samples for separating LAB. The kimchi samples were diluted ten times with a 0.85% saline solution, after which 0.1 ml of each sample was inoculated into an MRS agar (Difco MRS agar) plate containing 10 g of bacto-peptone, 10 g of meat extract, 5 g of yeast extract, 20 g of glucose, 1 g of Tween 80, 2 g of citric acid, 2 g of dipotassium phosphate, 5 g of sodium acetate, 0.1 g of manganese sulfate, 0.05 g of magnesium sulfate and 15 g of agar per 1 L distilled water and smeared with a glass rod. Subsequently, the plate was cultured for two days in a constant-temperature culture medium at 25° C. Each created colony was inoculated into an MRS agar plate and cultured at 25° C. for two days, thereby isolating 300 LAB colonies in total.

Isolation of LAB Inhibiting Growth of Kimchi Fermentation LAB

To select LAB inhibiting growth of kimchi fermentation LAB among the isolated 300 LAB, three types of kimchi fermentation indicator bacteria, *Leuconostoc* mesenteriodes (KCCM 11324), *Lactobacillus plantarum* (KCCM 11322) and *Lactobacillus sakei* (KCCM 40264), were inoculated into an MRS medium (Difco) containing 10 g of bacto-peptone, 10 g of meat extract, 5 g of yeast extract, 20 g of glucose, 1 g of Tween 80, 2 g of citric acid, 2 g of dipotassium phosphate, 5 g of sodium acetate, 0.1 g of manganese sulfate and 0.05 g of magnesium sulfate per 1 L distilled water and cultured at 25° C. for 24 hours.

The cultured cells were collected from the medium, washed twice with phosphate buffered saline (PBS, pH: 7.4), and suspended in 20% glycerol to be stored at −70° C., while the isolated 300 LAB colonies were inoculated into an MRS liquid medium and cultured at 25° C. for 24 hours, followed by centrifugal separation and suspending in 10% skim milk to be stored at −70° C.

Subsequently, 1% of the kimchi fermentation indicator bacteria was inoculated into an MRS agar medium and dried for 20 minutes, after which disk paper was placed thereon and 20 ml of a supernatant resulting from culture of each of the 300 LAB was dropped thereto, followed by culturing at 25° C. for 48 hours, thereby first selecting superior strains among bacteria forming an inhibiting ring. The first selected strains were second selected by the same method as mentioned above, thereby finally obtaining OH12, OH14, OH19, OH22, OK1 and OK2 which are excellent in inhibiting growth of harmful microorganisms.

Capabilities of the selected strains OH12, OH14, OH19, OH22, OK1 and OK2 to inhibit growth of the kimchi fermentation indicator bacteria of are listed in Table 1.

TABLE 1

| Strain | OH12 | OH14 | OH19 | OH22 | OK1 | OK2 | OH10 | OK4 |
|---|---|---|---|---|---|---|---|---|
| *Leuconostoc mesenteriodes* | + | + | + | + | + | − | − | + |
| *Lactobacillus plantarum* | + | + | + | − | + | + | − | − |
| *Lactobacillus sakei* | + | + | + | + |  | + | + | − |

In Table 1, + represents "inhibited" and − represents "uninhibited."

Table 2 illustrates results of antibacterial activity test of kimchi fermentation indicator bacteria.

TABLE 2

| | | Ingredients | | | |
|---|---|---|---|---|---|
| No. | Kimchi fermentation indicator bacteria | Mixed LAB culture fluid | A | B | C |
| 1 | *Weicella cibaria* | 22 | 14 | 0 | 0 |
| 2 | *Weicella cunfusa* | 23 | 13 | 0 | 0 |
| 3 | *Weicella koreensis* | 22 | 14 | 0 | 0 |

TABLE 2-continued

| No. | Kimchi fermentation indicator bacteria | Mixed LAB culture fluid | A | B | C |
|---|---|---|---|---|---|
| 4 | Leuconostoc citreum | 21 | 12 | 0 | 0 |
| 5 | Leuconostoc carnosum | 18 | 12 | 0 | 0 |
| 6 | Leuconostoc gasicomitatum | 25 | 14 | 0 | 0 |
| 7 | Leuconostoc gelidum | 23 | 12 | 0 | 0 |
| 8 | Leuconostoc kimchii | 24 | 14 | 0 | 0 |
| 9 | Leuconostoc lactis | 25 | 15 | 0 | 0 |
| 10 | Leuconostoc mesenteroides | 23 | 15 | 0 | 0 |
| 11 | Leuconostoc inhae | 18 | 12 | 0 | 0 |
| 12 | Lactobacillus sakei | 18 | 14 | 0 | 0 |
| 13 | Lactobacillus plantarum | 18 | 12 | 0 | 0 |
| 14 | Lactobacillus paraplantarum | 22 | 13 | 0 | 0 |
| 15 | Lactobacillus pentosus | 18 | 14 | 0 | 0 |
| 16 | Lactobacillus curvatus | 18 | 14 | 0 | 0 |
| 17 | Film yeast 1 | 21 | 13 | 0 | 0 |
| 18 | Film yeast 2 | 18 | 13 | 0 | 0 |
| 19 | Film yeast 3 | 17 | 13 | 0 | 0 |

*Unit: mm

In Table 2, numbers 1 to 16 represent kimchi fermentation indicator bacteria isolated during kimchi fermentation, identified by 16S rDNA analysis, numbers 17 to 19 are film yeasts (unidentified) isolated in a late stage of kimchi fermentation, which form scum on a surface in contact with the air, and ingredients A to C are commercially available antibiotic substances using antibacterial activity of LAB.

Identification of Selected LAB 16S rDNA sequences of the LAB selected in the isolation of LAB inhibiting growth of the kimchi fermentation bacteria were analyzed.

The inventors of the present invention named LAB OH22 "Lactobacillus plantarum OH22," deposited in the Korean Collection for Type Cultures as of Nov. 8, 2011 (accession number: KCTC12058BP).

LAB OH19 was named "Pediococcus pentosaceus OH19" and deposited in the Korean Collection for Type Cultures as of Nov. 8, 2011 (accession number: KCTC12057BP).

LAB OH12 was named "Lactobacillus casei OH12" and deposited in the Korean Collection for Type Cultures as of Nov. 8, 2011 (accession number: KCTC12055BP).

LAB OH14 was named "Lactobacillus paracasei OH14" and deposited in the Korean Collection for Type Cultures as of Nov. 8, 2011 (accession number: KCTC12056BP).

LAB OK1 was named "Lactobacillus sakei OK1" and deposited in the Korean Collection for Type Cultures as of Nov. 8, 2011 (accession number: KCTC12059BP).

LAB OK2 was named "Leuconostoc citreum OK2" and deposited in the Korean Collection for Type Cultures as of Nov. 8, 2011 (accession number: KCTC12060BP).

Preparation of Maturation-Delayed Kimchi

Chinese cabbages were salted to a salinity of 1.2 to 1.4%. 78.2% by weight (wt %) of the salted cabbages were mixed with kimchi seasonings including 6.0 wt % of white radish, 3.0 wt % of onion, 3.0 wt % of red pepper powder, 2.5 wt % of garlic, 0.7 wt % of ginger, 2.0 wt % of green onion, 0.6 wt % of sugar and 3.0 wt % of salted shrimp sauce.

Culture media obtained by culturing the selected six types of LAB, Lactobacillus plantarum OH22, Pediococcus pentosaceus OH19, Lactobacillus casei OH12, Lactobacillus paracasei OH14, Lactobacillus sakei OK1 and Leuconostoc citreum OK2, were mixed into a mixed LAB culture fluid, which was mixed with ingredients according to compositions listed in Table 3 and added to the kimchi.

Kimchi products mixed with the compositions in Table 3 were stored at 10° C. for 30 days and sampled at regular intervals, evaluating acidity, pH and total number of LAB of each kimchi product.

TABLE 3

| Example | Compositions |
|---|---|
| Example 1 | 0.8 wt % of vegetable LAB culture fluid + 0.2 wt % of purified water |
| Example 2 | 0.8 wt % of vegetable LAB culture fluid + 0.1 wt % of vitamin B1 + 0.1 wt % of purified water |
| Example 3 | 0.8 wt % of vegetable LAB culture fluid + 0.1 wt % of lactic acid + 0.1 wt % of purified water |
| Example 4 | 0.8 wt % of vegetable LAB culture fluid + 0.1 wt % of vitamin B1 + 0.1 wt % of lactic acid |
| Comparative Example 1 | 0.1 wt % of lactic acid + 0.8 wt % of purified water |
| Comparative Example 2 | 0.1 wt % of vitamin B1 + 0.8 wt % of purified water |
| Comparative Example 3 | 1.0 wt % of purified water |

Determination of Extent of Delayed Maturation of Kimchi

Measurement of Acidity (Storage for 30 Days)

Kimchi products mixed with the compositions according to Examples 1 to 4 and Comparative Example 1 to 3 were stored at 10° C. for 30 days and sampled at regular interval, followed by evaluation of acidity.

100 g of each of the kimchi products mixed with the compositions according to Examples 1 to 4 and Comparative Examples 1 to 3 was triturated and filtered with gauze to prepare a kimchi solution. Each kimchi solution was neutrally titrated with 0.1 N NaOH to a pH of 8.1, after which amount of used NaOH was converted into lactic acid content (%), thereby measuring acidity.

FIG. 1 is a graph illustrating acidities of the kimchi products mixed with the compositions according to Examples 1 to 4 and Comparative Examples 1 to 3 stored at 10° C. for 30 days.

Referring to FIG. 1, Comparative Example 1 shows acidity that increased in the early stage of storage and reached 1% on about the 15th day. Acidity of the kimchi product added with the mixed LAB culture fluid, vitamin B1 and lactic acid according to Example 4 was initially 0.51% and least increased to 0.67% after 30 days. The kimchi products to which the mixed LAB culture fluid was not added according to Comparative Examples 1 and 2 hardly have a maturation delaying effect, while the kimchi products to which the mixed LAB culture fluid, vitamin B1, lactic acid and purified water were added according to Examples 1 to 3 exhibit an insignificant maturation delaying effect.

Measurement of pH (Storage for 30 Days)

Kimchi products mixed with the compositions according to Examples 1 to 4 and Comparative Example 1 to 3 were stored at 10° C. for 30 days and sampled at regular interval, followed by evaluation of pH.

100 g of each of the kimchi products mixed with the compositions according to Examples 1 to 4 and Comparative Examples 1 to 3 was triturated and filtered with gauze to prepare a kimchi solution. Subsequently, a 20-ml sample of the kimchi solution was subjected to pH measurement using a pH meter (Mettler Toledo).

Figure 2:
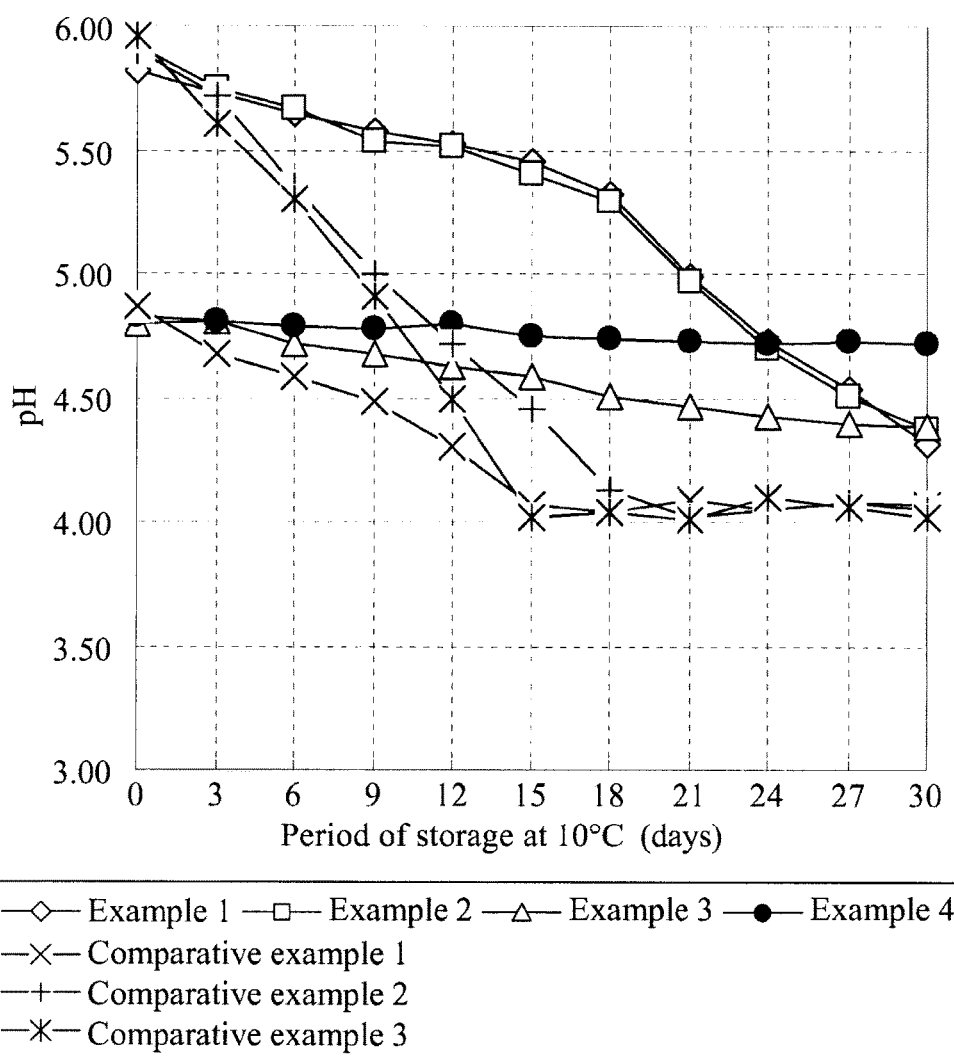
FIG. 2 is a graph illustrating pHs of the kimchi products mixed with the compositions according to Examples 1 to 4 and Comparative Examples 1 to 3 stored at 10° C. for 30 days.

FIG. 2 is a graph illustrating pHs of the kimchi products mixed with the compositions according to Examples 1 to 4 and Comparative Examples 1 to 3 stored at 10° C. for 30 days.

Referring to FIG. 2, Comparative Example 3 shows pH that decreased in the early stage of storage and stayed about 4.0 from about the 15th day. pH of the kimchi product added with the mixed LAB culture fluid, vitamin B1 and lactic acid according to Example 4 was initially 4.83 and least increased to 4.72 after 30 days. The kimchi products to which the mixed LAB culture fluid was not added according to Comparative Examples 2 and 3 hardly have a maturation delaying effect, while the kimchi products to which the mixed LAB culture fluid, vitamin B1, lactic acid and purified water were added according to Examples 1 to 3 exhibit an insignificant maturation delaying effect.

Measurement of Total Number of LAB (Storage for 30 Days)

Kimchi products mixed with the compositions according to Examples 1 to 4 and Comparative Example 1 to 3 were stored at 10° C. for 30 days and sampled at regular interval, followed by evaluation of total number of LAB.

100 g of each of the kimchi products mixed with the compositions according to Examples 1 to 4 and Comparative Examples 1 to 3 was triturated and filtered with gauze to prepare a kimchi solution. Each kimchi solution was diluted ten times with a 0.85% saline solution, after which 0.1 ml of the solution was inoculated into an MRS agar (Difco MRS agar) plate containing 10 g of bacto-peptone, 10 g of meat extract, 5 g of yeast extract, 20 g of glucose, 1 g of Tween 80, 2 g of citric acid, 2 g of dipotassium phosphate, 5 g of sodium acetate, 0.1 g of manganese sulfate, 0.05 g of magnesium sulfate and 15 g of agar per 1 L distilled water and smeared with a glass rod. Subsequently, the plate was cultured for two days in a constant-temperature culture medium at 25° C. Created colonies were counted and multiplied by a dilution rate, thereby measuring a number of LAB.

Figure 3:
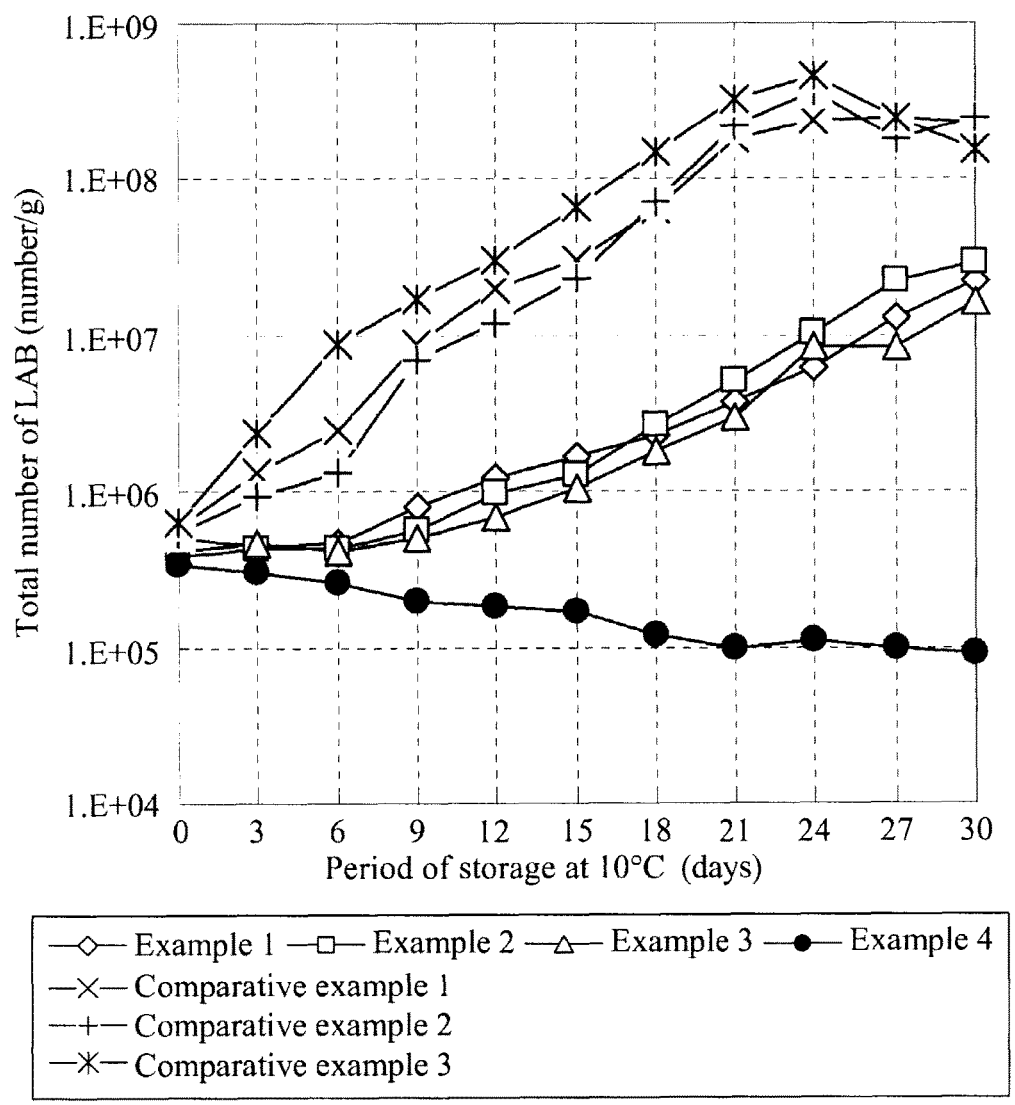
FIG. 3 is a graph illustrating total numbers of lactic acid bacteria (LAB) in the kimchi products mixed with the compositions according to Examples 1 to 4 and Comparative Examples 1 to 3 stored at 10° C. for 30 days.

FIG. 3 is a graph illustrating total numbers of LAB in the kimchi products mixed with the compositions according to Examples 1 to 4 and Comparative Examples 1 to 3 stored at 10° C. for 30 days.

Referring to FIG. 3, the kimchi product according to Comparative Example 3 shows vigorous growth of LAB from the early stage, whereas the kimchi product added with the mixed LAB culture fluid, vitamin B1 and lactic acid according to Example 4 has no increase in number of LAB. The kimchi products to which only vitamin B1 and lactic acid were added according to Comparative Examples 1 and 2 hardly have an effect of inhibiting growth of LAB, while the kimchi products to which the mixed LAB culture fluid, vitamin B1, lactic acid and purified water were added according to Examples 1 to 3 initially inhibited growth of LAB but did not suppress growth of LAB with time.

The foregoing examples show that a culture fluid composition including all of the mixed LAB culture fluid, vitamin B1 and lactic acid (Example 4) provides a remarkable kimchi maturation delaying effect.

Identification of Long-Term Kimchi Maturation Delaying Effect (90 Days)

The following experiment was carried out to identify a kimchi maturation delaying effect for a long period of storage. Example 4 having a superior kimchi maturation delaying effect and Comparative Example 3 were subjected to the same experiments as described above, except that a storage period was 90 days, evaluating acidity, pH and total number of LAB. Acidities, pHs and total numbers of LAB for 90-day storage were measured as in Table 4.

TABLE 4

| Duration of storage (days) | Acidity | | pH | | Total number of LAB | |
|---|---|---|---|---|---|---|
| | Example 4 | Comparative Example 3 | Example 4 | Comparative Example 3 | Example 4 | Comparative Example 3 |
| 0 | 0.52 | 0.28 | 4.78 | 5.61 | 3.5E+05 | 3.5E+05 |
| 7 | 0.47 | 0.28 | 4.96 | 5.70 | 1.5E+05 | 2.1E+06 |
| 14 | 0.50 | 0.73 | 4.97 | 4.97 | 2.4E+05 | 3.4E+07 |
| 21 | 0.52 | 1.11 | 4.87 | 4.11 | 7.1E+05 | 3.2E+08 |
| 28 | 0.50 | 1.19 | 4.87 | 4.02 | 8.5E+05 | 2.2E+08 |
| 35 | 0.61 | 1.34 | 4.88 | 4.10 | 1.2E+05 | 1.7E+08 |
| 42 | 0.63 | 1.34 | 4.85 | 4.10 | 1.4E+06 | 1.0E+08 |
| 49 | 0.64 | 1.32 | 4.83 | 4.07 | 7.4E+05 | 8.1E+07 |
| 56 | 0.64 | 1.32 | 4.83 | 4.08 | 4.9E+05 | 7.6E+07 |
| 63 | 0.63 | 1.32 | 4.82 | 4.08 | 4.8E+05 | 7.9E+07 |
| 70 | 0.62 | 1.31 | 4.81 | 4.01 | 3.2E+05 | 4.9E+07 |
| 77 | 0.61 | 1.30 | 4.81 | 4.01 | 3.8E+05 | 4.9E+07 |
| 84 | 0.60 | 1.30 | 4.76 | 3.99 | 3.7E+05 | 4.2E+07 |
| 91 | 0.63 | 1.30 | 4.73 | 3.99 | 4.5E+05 | 3.5E+07 |

Figure 4:
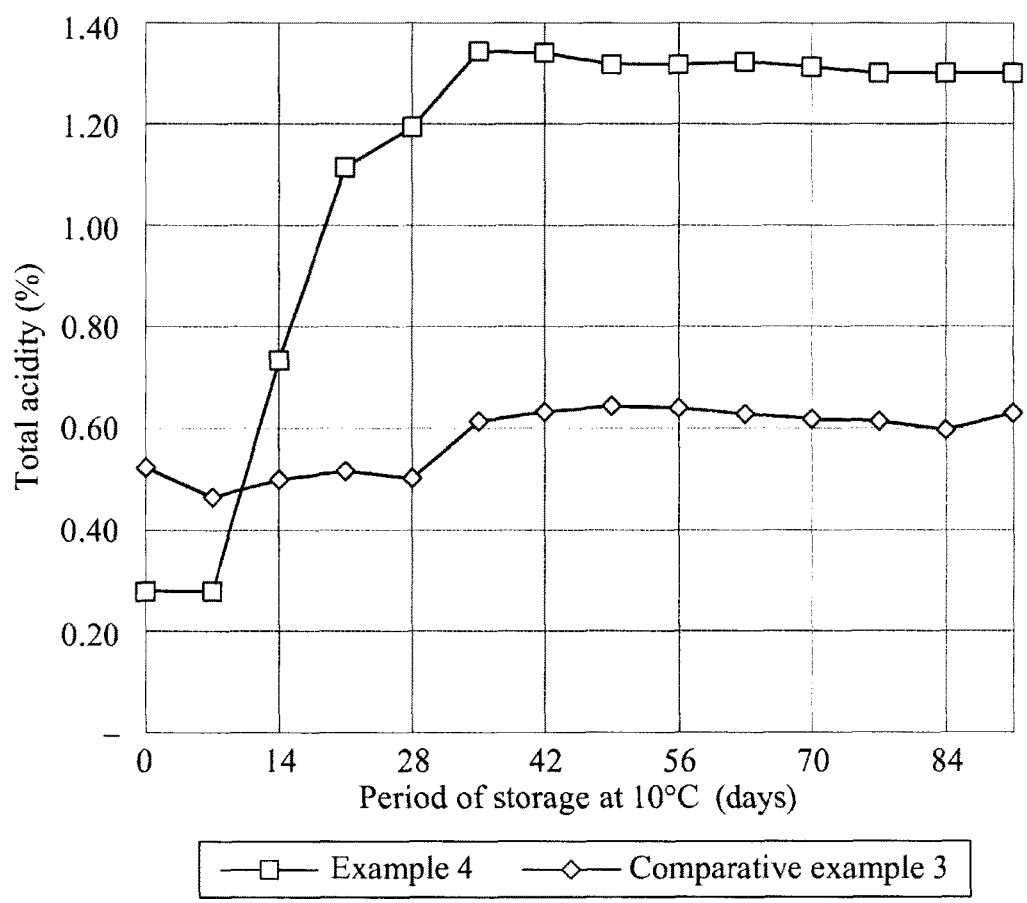
FIG. 4 is a graph illustrating acidities of the kimchi products mixed with the compositions according to Example 4 and Comparative Example 3 stored at 10° C. for 90 days.
Figure 5:
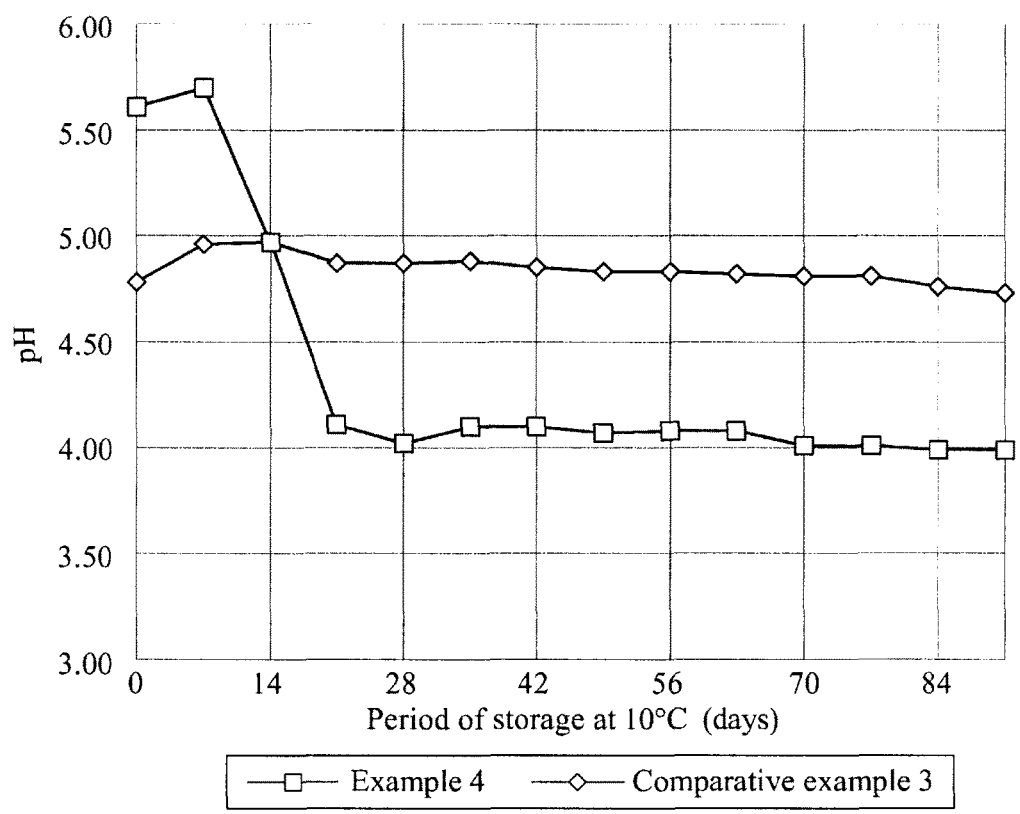
FIG. 5 is a graph illustrating pHs of the kimchi products mixed with the compositions according to Example 4 and Comparative Example 3 stored at 10° C. for 90 days.
Figure 6:
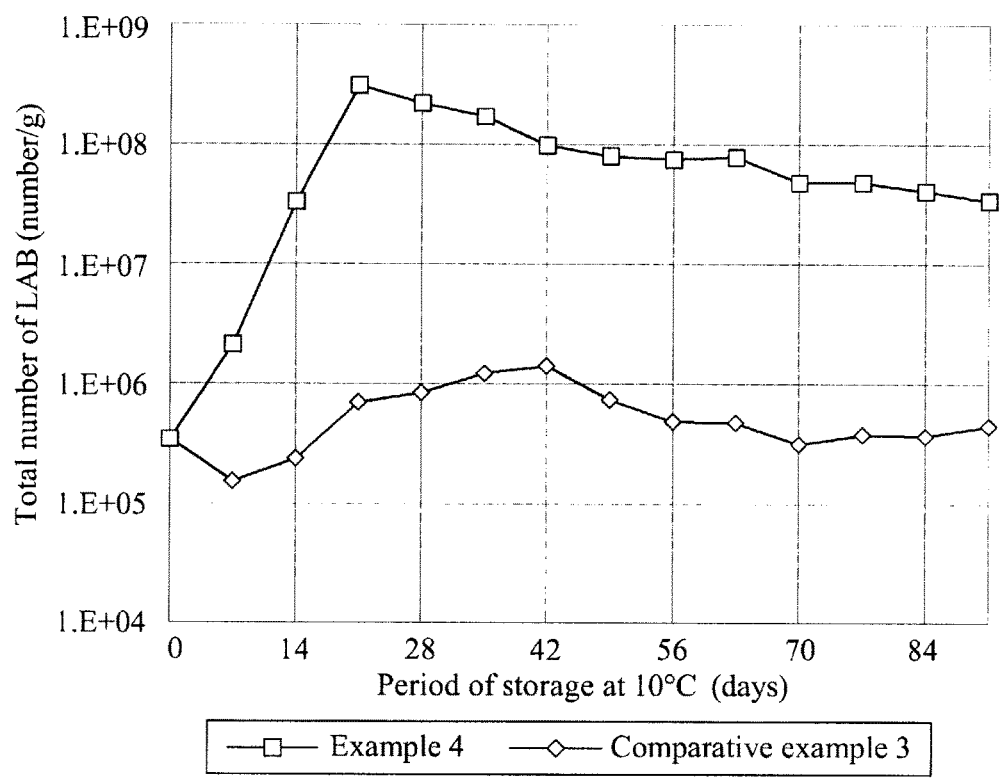
FIG. 6 is a graph illustrating total numbers of LAB in the kimchi products mixed with the compositions according to Example 4 and Comparative Example 3 stored at 10° C. for 90 days.

FIG. 4 is a graph illustrating acidities of the kimchi products mixed with the compositions according to Example 4 and Comparative Example 3 stored at 10° C. for 90 days. FIG. 5 is a graph illustrating pHs of the kimchi products mixed with the compositions according to Example 4 and Comparative Example 3 stored at 10° C. for 90 days. FIG. 6 is a graph illustrating total numbers of LAB in the kimchi products mixed with the compositions according to Example 4 and Comparative Example 3 stored at 10° C. for 90 days.

FIGS. 4 to 6 show that the kimchi product including all of the mixed LAB culture fluid, vitamin B1 and lactic acid according to Example 4 provides a remarkable kimchi maturation delaying effect for a long period of storage.

The invention claimed is:

1. A liquid culture composition for delaying maturation of kimchi comprising:
   a mixed lactic acid bacteria (LAB) liquid culture prepared by mixing culture media obtained by culturing respectively *Lactobacillus plantarum* OH22 with an accession number of KCTC12058BP, *Pediococcus pentosaceus* OH19 with an accession number of KCTC12057BP, *Lactobacillus casei* OH12 with an accession number of KCTC12055BP, *Lactobacillus paracasei* OH14 with an accession number of KCTC12056BP, *Lactobacillus sakei* OK1 with an accession number of KCTC12059BP, and *Leuconostoc citreum* OK2 with an accession number of KCTC12060BP;
   vitamin B1; and
   lactic acid;
   wherein the liquid culture composition comprises 1 to 40 parts by weight of the vitamin B1 and 5 to 40 parts by weight of the lactic acid based on 100 parts by weight of the mixed LAB liquid culture.

2. The liquid culture composition of claim 1, wherein the mixed LAB liquid culture comprises the culture media of each of the *Lactobacillus plantarum* OH22 with an accession number of KCTC12058BP, *Pediococcus pentosaceus* OH19 with an accession number of KCTC12057BP, *Lactobacillus casei* OH12 with an accession number of KCTC12055BP, *Lactobacillus paracasei* OH14 with an accession number of KCTC12056BP, *Lactobacillus sakei* OK1 with an accession number of KCTC12059BP, and *Leuconostoc citreum* OK2 with an accession number of KCTC12060BP in the same amount.

3. A method of making maturation-delayed kimchi, the method comprising:
- salting one or more kimchi ingredients selected from the group consisting of Chinese cabbage, white radish, summer radish and young radish; and
- mixing the salted kimchi ingredients with a liquid culture composition and a at least one seasoning selected from the group consisting of white radish, onion, red pepper powder, garlic, ginger, spring onion, white sugar and salted shrimp sauce,
- wherein the culture composition comprises a mixed lactic acid bacteria (LAB) culture, vitamin B1 and lactic acid, and
- the mixed lactic acid bacteria (LAB) liquid culture is prepared by mixing culture media obtained by culturing respectively *Lactobacillus plantarum* OH22 with an accession number of KCTC12058BP, *Pediococcus pentosaceus* OH19 with an accession number of KCTC12057BP, *Lactobacillus casei* OH12 with an accession number of KCTC12055BP, *Lactobacillus paracasei* OH14 with an accession number of KCTC12056BP, *Lactobacillus sakei* OK1 with an accession number of KCTC12059BP, and *Leuconostoc citreum* OK2 with an accession number of KCTC12060BP.

4. The method of claim 3, wherein the liquid culture composition comprises 1 to 40 parts by weight of vitamin B1 and 5 to 40 parts by weight of lactic acid based on 100 parts by weight of the mixed LAB liquid culture.

5. The method of claim 3, wherein the mixed LAB liquid culture comprises the culture media of each of the *Lactobacillus plantarum* OH22 with an accession number of KCTC12058BP, *Pediococcus pentosaceus* OH19 with an accession number of KCTC12057BP, *Lactobacillus casei* OH12 with an accession number of KCTC12055BP, *Lactobacillus paracasei* OH14 with an accession number of KCTC12056BP, *Lactobacillus sakei* OK1 with an accession number of KCTC12059BP, and *Leuconostoc citreum* OK2 with an accession number of KCTC12060BP in the same amount.

6. The method of claim 4, wherein the mixed LAB liquid culture comprises the culture media of each of the *Lactobacillus plantarum* OH22 with an accession number of KCTC12058BP, *Pediococcus pentosaceus* OH19 with an accession number of KCTC12057BP, *Lactobacillus casei* OH12 with an accession number of KCTC12055BP, *Lactobacillus paracasei* OH14 with an accession number of KCTC12056BP, *Lactobacillus sakei* OK1 with an accession number of KCTC12059BP, and *Leuconostoc citreum* OK2 with an accession number of KCTC12060BP in the same amount.

* * * * *